United States Patent

Provonchee

[11] Patent Number: 5,836,445
[45] Date of Patent: *Nov. 17, 1998

[54] POUCH

[75] Inventor: Richard B. Provonchee, Cushing, Me.

[73] Assignee: FMC Corporation, Philadelphia, Pa.

[21] Appl. No.: 685,228

[22] Filed: Jul. 23, 1996

[*] Notice: This patent issued on a continued prosecution application filed under 37 CFR 1.53(d), and is subject to the twenty year patent term provisions of 35 U.S.C. 154(a)(2).

[51] Int. Cl.$^6$ .................................................. B65D 25/08
[52] U.S. Cl. .......................... 206/221; 206/205; 220/371; 222/189.06
[58] Field of Search ..................................... 206/219, 205, 206/213.1, 484, 221, 823, 581; 383/38, 207, 209, 202, 200; 220/371; 222/129, 189.06, 94, 541.2; 229/87.05

[56] References Cited

U.S. PATENT DOCUMENTS

| | | |
|---|---|---|
| 2,015,972 | 10/1935 | Södergren . |
| 3,082,867 | 3/1963 | Gelpey .................................. 206/221 |
| 3,808,414 | 4/1974 | Roberts . |
| 4,310,118 | 1/1982 | Kisida et al. . |
| 4,927,405 | 5/1990 | Martin et al. . |
| 5,069,773 | 12/1991 | Frangioni . |
| 5,335,478 | 8/1994 | Aronsen . |
| 5,503,856 | 4/1996 | Hustad et al. . |

FOREIGN PATENT DOCUMENTS

| | | |
|---|---|---|
| 97202252.9 | 3/1998 | European Pat. Off. . |
| 294593 | 3/1915 | Germany . |
| 809427 | 2/1959 | United Kingdom . |
| 2272197 | 5/1994 | United Kingdom . |

*Primary Examiner*—Paul T. Sewell
*Assistant Examiner*—Nhan T. Lam
*Attorney, Agent, or Firm*—Polly E. Ramstad

[57] ABSTRACT

A flexible pouch having a filter. A multi-compartment flexible pouch having a common axis of radial symmetry and removable sealing means separating the compartments. A process for making a multi-compartment pouch having a common axis of radial symmetry.

19 Claims, 2 Drawing Sheets

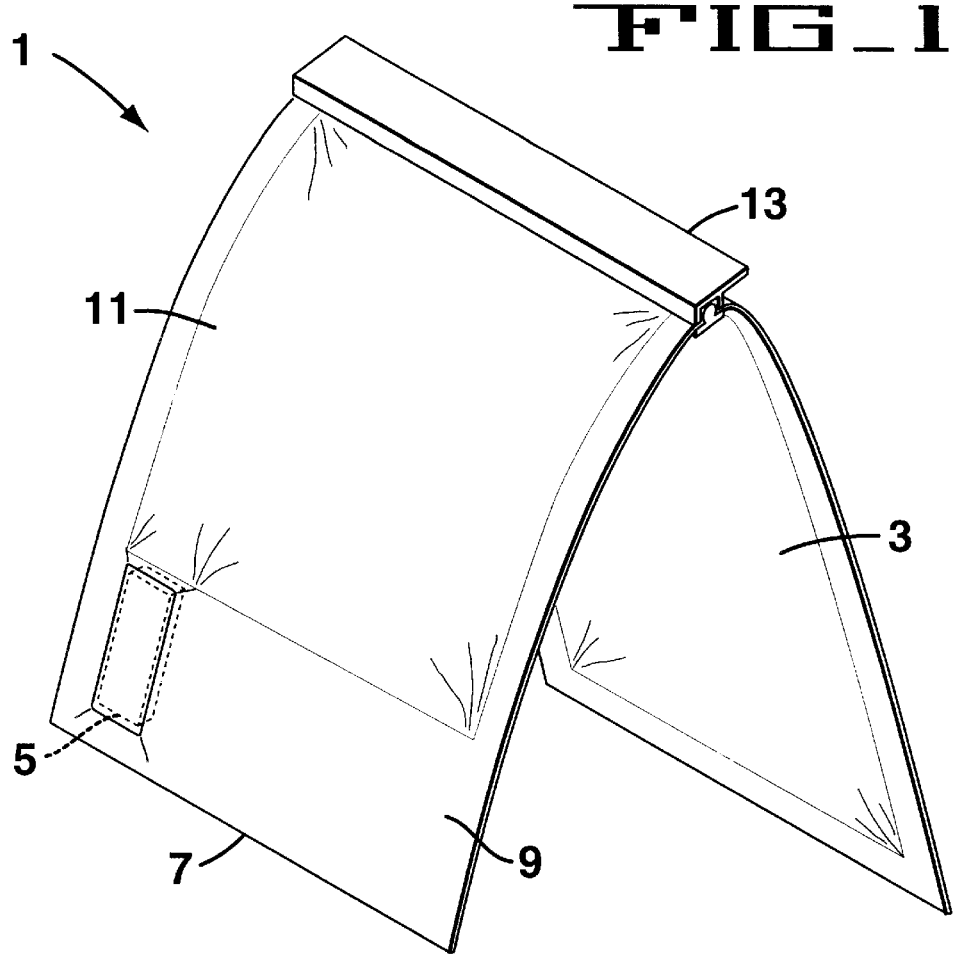
FIG_1
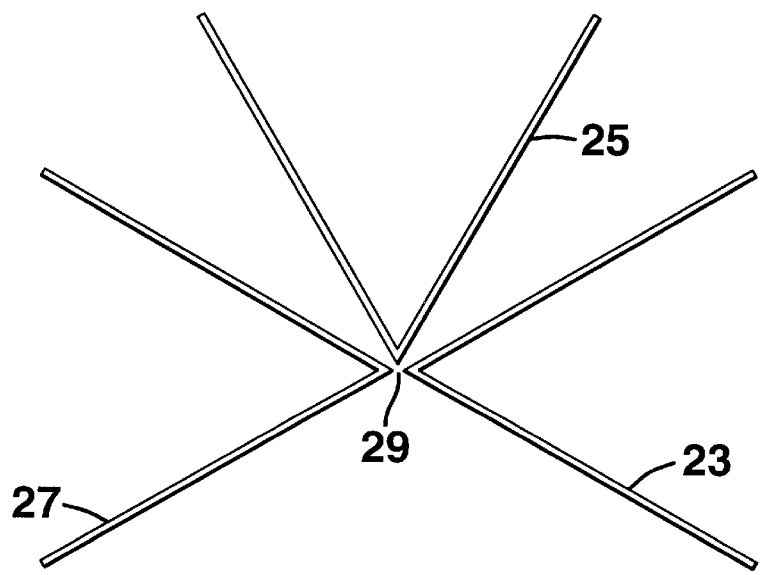
FIG_2

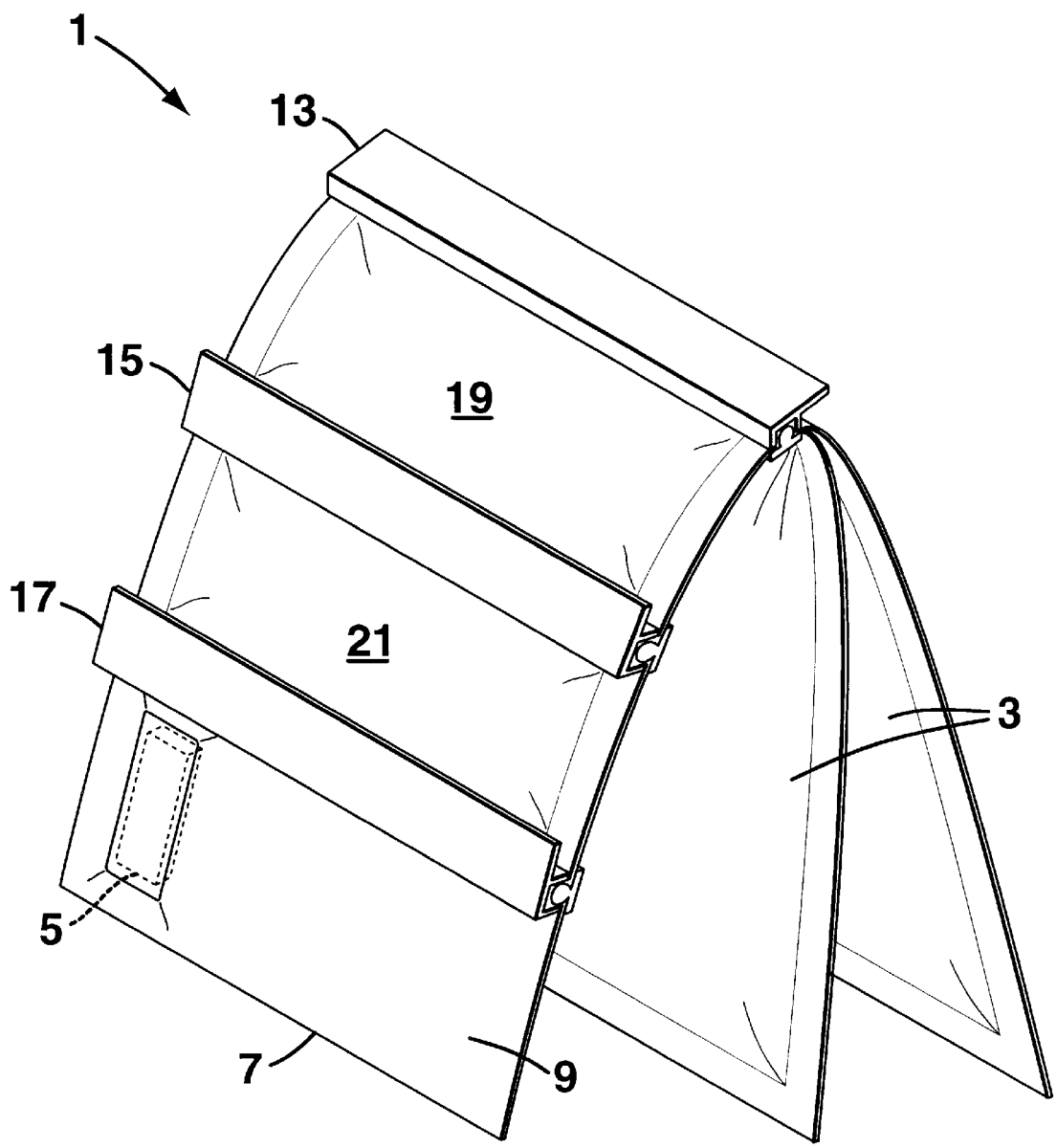
FIG_3

POUCH

FIELD OF THE INVENTION

This invention relates to a flexible air and water-impermeable pouch. More particularly this invention relates to a multi-compartment pouch which is air and moisture impermeable and which contains a filter in at least one compartment. This invention also relates to a process for making a multi-compartment pouch and a pouch containing a filter.

BACKGROUND OF THE INVENTION

When systems are sold in separate containers which have to be mixed together before use, the components of such systems are kept separate until such time as the system need be used. At that time, the components of the various containers are then opened and mixed. This mixing may occur in a vessel which is separate from the containers in which the components of the system are kept.

When one ore more of the components is a toxic material, unnecessary risk is encountered when the container for the toxic material need to be opened and mixed with other components of the system. In some instances, precautions, such as mixing the materials in a hood, need to be taken in order to minimize the risk. In other situations, protective clothing need to be worn to assure the safety of the individual who is conducting the mixing.

One method of reducing this risk is to provide a pouch which has been divided into separate compartments having burstible seals and then conducting the mixing in the pouch itself after bursting the seal between compartments. This method is cumbersome and requires the use of multiple seals.

Further, the various types of pouches sometimes contained compartments having solid material which needed to be mixed with a liquid material. When the contents of the pouch were discharged there was no way to assure that all of the contents of the solid material containing compartment would be dissolved in the liquid containing material. Sometime, these solid particles proved deleterious to the efficacy and use of the contents of the pouch. There was no procedure disclosed for assuring that the final system to be used would not be contaminated with small particles of material.

British patent 2,272,197 is directed to a two-compartment pouch wherein each compartment has separate filling me s for that compartment. The British patent discloses a three or four-compartment package but fails to teach or suggest how such a package could be constructed. Additionally, the British patent fails to teach or suggest the presence of a filter so that solid particles could be removed from the system prior to using the system as it comes from the pouch.

U.S. Pat. No. 5,069,773 is directed to an apparatus and method for forming an electrophoretic gel having a polymer. The '773 Patent discloses a multi-compartment pouch which is construed so that a two-layered pouch is divided into compartments by means of burstable seals.

None of the prior art teaches or suggests a multi-compartment pouch which has a common axis of radial symmetry an wherein only a single removable means is necessary to seal all of the compartments from one another. Further, none of the prior art teach or suggest such a multi compartment pouch wherein any of the compartments may be further divided into additional compartments by placing removable sealing means across the width of the compartment. Finally, the prior art fails to teach or suggest a pouch having a filter therein.

BRIEF DESCRIPTION OF THE DRAWINGS

FIG. 1 is a perspective view of a two compartment pouch with a filter.

FIG. 2 is a schematic representation of the order of folding barrier material to make a multi-compartment pouch.

FIG. 3 is a perspective view of a multi-compartment pouch with a filter, removable sealing means and a component divided into three compartments by removable sealing means.

SUMMARY OF THE INVENTION

Broadly, this invention contemplates a flexible water and air impermeable pouch comprising a filter immovably disposed inside of the pouch and at one end thereof.

This invention also contemplates a multi-compartment flexible pouch comprising at least three flexible compartments, each of said compartments being separated from the other compartments, each compartment having walls independent of the walls of any other compartment, all of said compartments having a common interchange with the axis of radial symmetry around the common interchange being parallel to the surfaces of each compartment.

This invention also contemplates a process for preparing a multi-compartment pouch comprising folding a first sheet of barrier material in half along its' width, folding a second sheet of barrier material in half along its' width. Joining a folded part of the first sheet with a folded part of the second sheet, folding successive sheets in half along the sheet width and joining the folded part of each successive sheet with the folded part of the next sheet, and joining a folded part of the last sheet with a folded part of the first sheet, said folding taking place to form a multi-compartment pouch having a common interchange with the axis of radial symmetry around the common interchange being parallel to the surface of all the compartments.

DETAILED DESCRIPTION OF THE INVENTION

In the specification and claims, the term "barrier material" is used. The barrier material is the material from which the pouch (FIG. 1, generally indicated as 1) and any compartments 3 is constructed. The barrier material may be a single layer or a laminated structure. The nature of the barrier material is dictated by the material to be contained in the pouch and the conditions of storage prior to use. Barrier materials and their properties are well known in the art.

In one embodiment, a barrier material is folded on itself and is sealed on three sides, leaving an opening in which the filter 5 is to be inserted. When the filter 5 is inserted, it is generally inserted so that one end of the filter 5 is at the end 7 of the pouch through which material may be discharged.

The filter 5 may be placed into the compartment 9 which is coextensive with the length of the filter 5. Compartment 9 is preferably sealed so that material from the compartment 11 must pass through the filter 5 when it is discharged out of the pouch 1.

The compartment 11 may be filled either prior to inserting the filter 5 and sealing the compartment 9 next to the filter 5 or by leaving an unsealed port in the compartment 11 and filling the compartment 11 through this unsealed port and thereafter sealing the port.

The material may be discharged from the compartment 11 by cutting the seal in the area of the filter 5, or by providing a burstable seal around the filter. The opening to discharge material is preferably coextensive with the perimeter of the filter 5 to assure that material will be discharged through the filter 5 and not from around the filter 5.

When reference is made to sealing the barrier material, the method may be chosen from one of many known in the art. Heat sealing is one of the more commonly used methods whereby heat is used to fuse the barrier material to itself and thereby form a seal. Adhesive joining, whereby an adhesive is applied to one or both surfaces to be sealed prior to sealing, may also be used.

When reference is made to compartments 3 within a pouch 1, the term is used in the sense of separate sections within the pouch 1. Said sections may be physically demarcated such as by removable seals 13 or burstable seals (not shown) or said sections may be demarcated by what they contain such as when a pouch 1 contains a snug fitting filter 5 at one end 7, of the filter compartment 9, and contains the material to be filtered in the rest of the pouch 1, the material compartment. Of course, a multi-compartment pouch may have compartments demarcated by a combination of the above.

The barrier material is formed into a pouch which is sectioned into two communicating compartments, (3 and 11 of FIG. 1) and a filter compartment 9 which contains a filter 5. The other compartments contain a material which it is desired to filter prior to use. The filter compartment 9 is generally sized so as to assure that material passing through the filter compartment 9 will pass through the filter 5 and not pass around the filter. The material containing compartments may be held non communicating with the filter 5 containing compartment 9 and from each other by a removable seal 13 (FIG. 1 or 13, 15, 17 of FIG. 3) or a burstable seal or the like until the filter 5 is used.

In making a multi-compartment pouch 1 of this invention, (FIG. 2 is a schematic representation of the order of folding barrier material to form a multi-compartment pouch) a first sheet 23 of barrier material is folded in half across its width. A second similar sized sheet 25 of barrier material is folded in half across its width and is superimposed on the first folded sheet 23, maintaining the same orientation with respect to the position of the fold. The half of the first sheet 23 and the half of the second sheet 25 that are in contact with each other are sealed to each other along the two sides which are perpendicular to the fold. A third similar sized sheet 27 of barrier material is folded in half across its width and is superimposed on the first two sheets, maintaining the same orientation with respect to the position of the fold. The half of the second sheet 25 and the half of the third sheet 27 that are in contact with each other are sealed to each other along the two sides which are perpendicular to the fold. The first sheet 23 and the last sheet 27 are unfolded and the unsealed half of the first sheet 23 is sealed to the unsealed half of the last sheet 27 along the two sides which are perpendicular to the fold lines. A multi-compartment pouch so formed will have three compartments, each of said compartments being separate from the other compartments, each compartment having walls independent of the walls of any other compartment, all of said compartments having a common interchange 29 with the axis of radial symmetry around the common interchange 29 being parallel to the surfaces of each compartment.

Although the first and last sheets 23 and 27 are folded in half for the purpose of clarity in the above description, it should be understood that the first and last sheets 23 and 27 need not be folded. Although the process of making a multi-compartment pouch has been described in terms of making the pouches one at a time using sheets of barrier material, it should be understood that adapting the above process to continuous pouch making is well within the scope of one skilled in the art. Although the process of making a multi-compartment pouch has been described in terms of making three equal sized compartments, it should be understood that the above process may be used to make a four, five, six or more compartment pouch and that the compartments so made need not be of equal size.

One of the advantages of a multi-compartment pouch 1 of this invention is that each compartment communicates with each of the other compartments through a common interchange 29. Thus, a single removable sealing means 13 or a single burstable sealing means (not shown) placed at said common interchange 29 can effect a seal between all of the compartments 3 and 19 (FIG. 3) of said multi-compartment pouch 1.

Another advantage of a multi-compartment pouch 1 of this invention is that the pouch may be more compact than a conventional multi-compartment pouch with a similar number of compartments of similar volume. Looked at simply, when a conventional multi-compartment pouch is laid flat on a surface such that the surfaces of the compartments of the pouch are parallel with the surface said pouch is laid out on, the area covered by the pouch is the sum of the area covered by each of the individual compartments. When a multi-compartment pouch of this invention is laid out in a similar fashion, the area covered by said pouch is the sum of the areas covered by the individual compartments less the area of one or more of the compartments that are superimposed, whereby only the largest of said superimposed compartments contribute to the total area covered by the pouch. This advantage is of particular value when storing the pouches and when the pouches must be manipulated.

In one embodiment, (FIG. 3) one or more compartments of a multi-compartment pouch 1 if this invention may be divided into two or more compartments (19, 21 and 9 of FIG. 3) by methods known in the art such as burstable seals or external clamping means (13, 15 and 17 of FIG. 3) or the like.

In another embodiment, at least one of the compartments 9 (FIG. 1) of a multi-compartment pouch of this invention contains a filter 5, said compartment 9 with filter 5 being positioned so that material in the pouch passes through the filter prior to leaving the pouch. Suitable filter materials are well known in the art such as glass wool, open cell urethane foam, porous plastic, bonded polyolefin and the like.

A filter 5 may be inserted in any one of the compartments (9 of FIG. 1 and 3 of FIGS. 1 and 3). The filter 5 is inserted into the compartment 9 (FIGS. 1 and 3), if it is an elongated filter, so that one end of the filter 5 is at the end of the compartment 7 which will subsequently be sealed. The compartment 9 coextensive with the length of the filter 5 is then sealed so that material exiting the pouch 1 from the various compartments (11 and 3 of FIGS. 1 and 3, 19 and 21 of FIG. 3) will pass through the filter 5 as the materials leave the pouch, or, if premixed, the mixture will pass through the filter.

A removable clip 13, (FIGS. 1 and 3) and 15 and 17 (FIG. 3) or other suitable sealing means is then placed on the axis of radial symmetry common to all the compartments. This will separate the compartments until such time as it is desired to mix the contents of the compartments together and to filter them, if filtering is provided for.

The compartments are then filled, through the open end, with the different materials and are then heat-sealed.

In order to more fully illustrate the nature of this invention and the manner of practicing the same the following example is presented.

EXAMPLE

A three-compartment pouch containing a cellulose acetate filter is constructed from three sheets of barrier material as described above. The compartment containing the filter is divided into two additional compartments by means of removable clip intermediate the length of the compartment and across its width. The divided compartment is separated from the remainder of the compartment, which contains the filter and which is sealed coextensive with the length of the filter, by means of a removable clip disposed across the width of the filter containing compartment.

After the pouch and its three compartments have been formed, the compartments are filled with material as follows. The invention will be illustrated by means of a multi-component electrophoresis composition. With a removable clip in place across the axis of radial symmetry, which is common to all of the compartments, is placed the following. 31 g of urea is placed in the open end of one compartment and the compartment is then heat-sealed. 50 microliters of N,N,N',N'-tetramethyl ethylenediamine (TEMED) and 42 mls of a buffer is placed in the open end of a second compartment and the compartment is heat-sealed.

The third compartment has been divided into two additional compartments by means of a removable clip disposed across the width of the compartment and intermediate its length. The lower compartment of the divided compartment is filled through a port in the seal along the perimeter. The lower compartment is filled with 38 mg of ammonium persulfate initiator. The compartment above the clip, the initiator containing compartment, is filled with 8.5 mls of a 50% solution of acrylamide. A removable clip is then placed across the compartment and above the acrylamide containing portion. The clip effectively separates the acrylamide containing portion from the top portion of the full compartment. A filter is then placed into the top portion of the compartment so that one end of the filter is at the area to be heat-sealed when the compartment is heat-sealed. The area next to the filter, and coextensive with its' length, is then heat-sealed and the remainder of the compartment is heat-sealed.

When the pouch is to be used to create an electrophoretic gel, it is accomplished in the following manner. The pouch is allowed to come to room temperature. The removable clip which is along the common axis is removed so that all the contents of the compartments may be mixed with one another, except for the acrylamide containing compartment which is separated by a removable seal from the other compartments and from the initiator containing compartment. The contents of the pouch are mixed by hand for one minute. The pouch is placed on an Orbital® shaker for five minutes at medium speed. The contents of the compartments, except for the segregated acrylamide containing compartment are again mixed by hand for one minute. The pouch is then placed on a shaker for five more minutes. Now, the removable clip which separates the acrylamide from the remainder of the components is removed and the pouch is mixed well by hand for one minute. The removable clip which separates the filter from the pouch contents, is then removed.

All of the contents of the various compartments are now drained into the compartment containing the filter and the pouch is folded in half at a predetermined line. The filter containing compartment and the remainder of the pouch are then tipped upward and a corner of the compartment containing the filter is cut to expose the filter and the contents to the atmosphere and to allow the contents to be dispensed. The solution is then dispensed through the filter into a container by gently squeezing the pouch to achieve optimal flow through the filter. The container with the solution is allowed to stand for at least two hours to achieve polymerization.

The use of a filter in a multi-compartment pouch is affective to remove any residual solids and to prevent possible contamination. The filter restricts the flow of material to allow for better filling of narrow spaces when material is being dispensed from the pouch and through the filter.

While this invention has been described in terms of preferred embodiments and illustrated by means of a specific example, the invention is not to be construed as limited except as set forth in the following claims.

I claim:

1. A flexible water and air impermeable pouch including a filter compartment and a filter immovably disposed therein, with an area on one side thereof exposed to the interior of the pouch, the filter compartment is adapted to have an opening formed in an area adjacent a portion of the filter contiguous with the exterior of the pouch, and the filter is adapted to filter fluid exiting the pouch through the opening.

2. A pouch according to claim 1 wherein the pouch comprises two flexible sheets of barrier material or one flexible sheet of barrier material folded on itself, said sheets or folded sheet having the perimeter of each sheet or folded sheet sealed to one another said filter having an exit end, and the area adjacent the exit end of the filter sealed with a breakable or cutable seal.

3. A pouch according to claim 2 wherein the pouch contains a material therein to be dispensed through the filter.

4. The pouch of claim 1 further comprising a removable barrier disposed between the filter compartment and the interior of the pouch.

5. A flexible water and air impermeable pouch, as recited in claim 1, said pouch further comprising at least two interconnectable compartments each of said interconnectable compartments being separated from the other compartments by a removable barrier.

6. A flexible water and air impermeable pouch, as recited in claim 5, comprising at least three interconnectable compartments, all separated by a single removable barrier.

7. A flexible water and air impermeable pouch, as recited in claim 6, wherein one of said separable compartments is further subdivided in to at least two sub-compartments by at least one additional removable barrier.

8. A flexible water and air impermeable pouch, as recited in claim 6, wherein at least one of said barriers comprise a removable scaling means disposed across at least one of said interconnected compartments along a line of interconnection therebetween.

9. A flexible water and air impermeable pouch, as recited in claim 5, wherein said filter compartment is separated from one of said interconnecting compartments by an additional removable barrier.

10. A process for preparing a multi-compartment pouch comprising folding a first sheet of barrier material in half along its width, folding a second sheet of barrier material in half along its width, joining a folded part of the first sheet with a folded part of the second sheet, folding successive sheets in half along the sheet width and joining the folded part of each successive sheet of barrier material with the folded part of the next sheet of barrier material, and joining a folded part of the last sheet with a folded part of the first sheet, said folding taking place to form an axis of radial symmetry around an interchange common to all the compartments.

11. A process according to claim 10 comprising sealing each of the compartments on two sides thereof, removably sealing each of the compartments at the common axis thereof, filling each compartment with material at the non-sealed side thereof, and sealing the side of the compartment where filling has occurred.

12. A process according to claim 11 comprising inserting a filter in an immovable manner in one compartment and at the end of the compartment remote from the axis of radial symmetry, sealing the area next to the filter and coextensive with the length of the filter, removing the sealing means from the axis of radial symmetry, mixing the contents of the compartments with one another, opening the compartment having the filter at the perimeter of the filter and discharging the mixed contents of the pouch through the filter.

13. A process according to claim 10 comprising inserting a filter in at least one compartment and at the end of the compartment remote from the axis of radial symmetry and sealing the area next to the filter and coextensive with the length of the filter whereby said filter is immovable in said sealed area.

14. A process according to claim 10 comprising forming a pouch having three compartments.

15. A process according to claim 10 comprising dividing one compartment into at least two non-communicating compartments by placing removable sealing means across the width and intermediate the length of the compartment being divided.

16. A flexible multi-compartment pouch comprising at least three exterior flexible interconnectable compartments, each of said compartments being separated from the other compartments, each compartment having walls independent of walls of any other compartment, all of said compartments having a common interchange with the axis of radial symmetry around the common interchange being parallel to the surfaces of each compartment said pouch comprising a plurality of sheets of barrier material, including a first sheet of barrier material a last sheet of barrier material and intermediate said first and last sheets at least one folded sheet of barrier material, wherein (a) a first compartment comprises one side thereof from a first portion of said first sheet of barrier material, and the other side thereof from a first folded portion of an intermediate folded sheet of barrier material, (b) a second compartment comprises one side thereof from a second folded portion of an intermediate folded sheet of barrier material and a first portion of said last sheet of barrier material and (c) a third compartment comprises one side thereof from a second portion is of said last sheet of barrier material and the second portion of said first sheet of barrier material.

17. A flexible water and air impermeable pouch, as recited in claim 16, comprising three interconnectable compartments.

18. A flexible water and air impermeable pouch, as recited in claim 16, wherein at least one of said compartments is divided into two subcompartments by a removable sub-compartment barrier, the first of said sub-compartments adjoining said common interchange and the second of said sub-compartments being selectively separated therefrom by said removable sub-compartment barrier.

19. A method of making a multi-compartment container comprising:

(a) providing a first and last sheet and of barrier material each having two sections separated by a section dividing line;

(b) providing at least one additional sheets of barrier material, said additional sheets being folded into first and second sections;

(c) placing said sheets so that the folded sections of said at least one additional sheet and the first sections of said first and last sheets overlie one another with said at least one additional sheet interposed between said first and last sheets, and all of said section separating and fold lines also overlying one another; and (d) placing said second sections of said first and last sheets adjacent one another to form a first compartment, and sealing together the perimeters of said adjacent sheet section and the perimeters of successive pairs of adjacent sections of adjacent sheets, such that said sealed perimeters, together with said fold and section separating lines form compartments between each of said sealed adjacent sheet sections.

* * * * *